US011253408B2

United States Patent
Rhodes et al.

(10) Patent No.: US 11,253,408 B2
(45) Date of Patent: Feb. 22, 2022

(54) REFASTENABLE DISPOSABLE GARMENT HAVING A CURLED EDGE, AND PROCESS FOR MAKING SAME

(71) Applicant: Kimberly-Clark Worldwide, Inc., Neenah, WI (US)

(72) Inventors: Brian K. Rhodes, Winneconne, WI (US); Suzanne M. Schmoker, Oshkosh, WI (US); Kimberly L. Ellefson, Oshkosh, WI (US); Julie A. Paveletzke, Appleton, WI (US); Kimberly M. Downs, Ripon, WI (US); Brent C. Otis, New London, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 512 days.

(21) Appl. No.: 16/440,581

(22) Filed: Jun. 13, 2019

(65) Prior Publication Data
US 2019/0290508 A1    Sep. 26, 2019

Related U.S. Application Data

(62) Division of application No. 13/336,006, filed on Dec. 23, 2011, now Pat. No. 10,363,176.

(51) Int. Cl.
*A61F 13/56*    (2006.01)
(52) U.S. Cl.
CPC .. *A61F 13/5644* (2013.01); *A61F 2013/5677* (2013.01)

(58) Field of Classification Search
CPC .......... A61F 13/5644; A61F 2013/5677; A61F 13/15756; A61F 13/56
See application file for complete search history.

(56) References Cited

U.S. PATENT DOCUMENTS

| | | | |
|---|---|---|---|
| 5,288,546 | A | 2/1994 | Roessler et al. |
| 5,383,872 | A | 1/1995 | Roessler et al. |
| 5,549,591 | A | 8/1996 | Landvogt |
| 5,944,707 | A | 8/1999 | Ronn |

(Continued)

FOREIGN PATENT DOCUMENTS

| | | |
|---|---|---|
| EP | 1829513 A2 | 9/2007 |
| EP | 2286778 B1 | 6/2014 |

*Primary Examiner* — Michele M Kidwell
(74) *Attorney, Agent, or Firm* — Kimberly-Clark Worldwide, Inc.

(57) ABSTRACT

A refastenable disposable garment defines a longitudinal direction and a transverse direction, and comprises a first waist region contiguous with a first waist edge. The first waist region defines first and second side edges transversely spaced apart and defines first and second surfaces. The first waist region is elastomeric proximal both the first and second side edges. The garment can include a second waist region and a crotch region that interconnects the first and second waist regions. The garment comprises non-extensible, relatively rigid first and second fastening components attached to the first surface of the first waist region adjacent the first and second side edges, respectively. The first waist region defines first and second flange portions transversely outward of the first and second fastening components, respectively. Each flange portion is transversely curled toward the second surface. A process for making such an article is also disclosed.

10 Claims, 7 Drawing Sheets

(56) References Cited

U.S. PATENT DOCUMENTS

| | | |
|---|---|---|
| 6,193,703 B1 | 2/2001 | Jackson |
| 6,213,991 B1 * | 4/2001 | Kling .................. A61F 13/5633 |
| | | 604/385.01 |
| 6,447,497 B1 | 9/2002 | Olson |
| 6,461,343 B1 | 10/2002 | Schaefer et al. |
| 6,562,167 B2 | 5/2003 | Coenen et al. |
| 6,671,935 B2 | 1/2004 | Filion et al. |
| 7,288,079 B2 | 10/2007 | Toyoshima et al. |
| 7,455,665 B2 | 11/2008 | Wendelstorf et al. |
| 7,765,614 B2 | 8/2010 | Takino et al. |
| 8,734,417 B2 | 5/2014 | LaVon et al. |
| 9,724,251 B2 * | 8/2017 | LaVon ................ A61F 13/5622 |
| 2003/0055394 A1 | 3/2003 | Gibbs |
| 2003/0125702 A1 | 7/2003 | Couture-Dorschner et al. |
| 2005/0131378 A1 | 6/2005 | Sasaki et al. |
| 2005/0175269 A1 | 8/2005 | Ashton et al. |
| 2007/0250029 A1 | 10/2007 | Popp et al. |
| 2009/0254059 A1 | 10/2009 | Nilsson et al. |
| 2010/0004616 A1 | 1/2010 | Nakamura et al. |
| 2011/0071489 A1 | 3/2011 | Kinoshita et al. |
| 2011/0094661 A1 | 4/2011 | Thorson |

\* cited by examiner

REFASTENABLE DISPOSABLE GARMENT HAVING A CURLED EDGE, AND PROCESS FOR MAKING SAME

BACKGROUND

People rely on disposable absorbent garments in their everyday lives, including such garments as adult incontinence products, enuresis pants, training pants, and diapers. In certain cases, it is desirable that garments are refastenable about the wearer. For example, underwear-style garments, such as disposable incontinence underwear or toileting training pants, include refastenable fastening systems. For instance, in certain circumstances, it might be more convenient to remove and replace a donned garment when there is a desire not to have to remove the wearer's clothing and shoes.

With certain refastenable garments, such as adult incontinence underwear and enuresis pants, it is important that the garments look and feel as much as possible like "regular" underwear to promote an improved sense of normalcy to the wearer who suffers from incontinence or enuresis. Accordingly, there is a desire in certain cases to incorporate fastening systems in garments in such a way that the fastening system is relatively discreet in order to make the garment more like "regular" cloth underwear. One possible approach is to provide at least one garment-like, refastenable seam, provided by one or more strips of mechanical fastening material, such as a hook-and-loop style fastener. However, one potential drawback to such designs is that a garment-like refastenable seam may be difficult to detect and difficult to manipulate by the user of the product. In particular embodiments, when a fastener which lies relatively close to an edge of the base substrate to which it is applied, it can in some cases be difficult to locate the edge of the refastenable seam, and, once located, it can in some cases be difficult to grasp the edge of the refastenable seam so as to disengage the seam to allow the product to be opened and inspected or removed.

It is also frequently desirable to incorporate elastomeric materials in disposable absorbent garments to enhance fit and performance. What is needed is a refastenable disposable absorbent garment having elastomeric properties, and having a refastenable seam or fastening portion that is garment-like yet easy to see and/or easy to grasp. Further, a method of making such a garment is also needed.

SUMMARY OF THE INVENTION

In one aspect, the present invention is directed to a refastenable disposable absorbent garment. In one embodiment of the garment aspect of the invention, garment defines a longitudinal direction and a transverse direction, and defines longitudinally spaced apart first and second waist edges extending generally in the transverse direction. The garment further comprises a first waist region contiguous with the first waist edge. The first waist region defines first and second side edges spaced apart in the transverse direction and defines opposed first and second surfaces. The first waist region is elastomeric proximal both the first side edge and the second side edge of the first waist region. The garment further comprises a second waist region contiguous with the second waist edge. The second waist region defines first and second side edges spaced apart in the transverse direction. The garment further includes a crotch region that extends between and interconnects the first and second waist regions. The garment further comprises a non-extensible, relatively rigid first fastening component attached to the first surface of the first waist region adjacent its first side edge, and further comprises a non-extensible, relatively rigid second fastening component attached to the first surface of the first waist region adjacent its second side edge. The first and second fastening components each have a length. The first waist region defines a first flange portion transversely outward of the first fastening component and also defines a second flange portion transversely outward of the second fastening component. The first flange portion is transversely curled toward the second surface of the first waist region along a first flange portion curled length, and the second flange portion is transversely curled toward the second surface of the first waist region along a second flange portion curled length. Preferably, the first surface is a body-facing surface.

In another aspect, the present invention is directed to a process for making a refastenable disposable absorbent garment. In one embodiment of the process aspect of the invention, the process includes making a garment that defines a longitudinal axis extending in a longitudinal direction and a transverse axis extending in a transverse direction, the garment further comprising longitudinally spaced apart first and second waist edges extending generally in the transverse direction. The process comprises providing an elastomeric waist panel web; stretching the elastomeric waist panel web by at least 10% to create a stretched waist panel web; attaching a non-extensible, relatively rigid first fastening component to the stretched waist panel web; severing the waist panel web adjacent the first fastening component to create a first waist region first portion; and incorporating the first waist region first portion into a first waist region of the garment. Within the garment, the first waist region is contiguous with the first waist edge. The first waist region defines a first side edge extending in the longitudinal direction and defines opposed first and second surfaces. The first waist region is elastomeric proximal the first side edge of the first waist region. The first fastening component is attached to the first surface of the first waist region adjacent its first side edge, and the first fastening component has a length. The first waist region defines a first flange portion transversely outward of the first fastening component. The first flange portion is transversely curled toward the second surface of the first waist region along a first flange portion curled length. In a preferred embodiment, the process further comprises attaching a non-extensible, relatively rigid second fastening component to the stretched waist panel web; severing the waist panel web adjacent the second fastening component to create a first waist region second portion; and incorporating the first waist region second portion into the first waist region of the garment.

DETAILED DESCRIPTION OF EXEMPLARY EMBODIMENTS

The present invention relates to a refastenable disposable garment having a curled edge, and to a method of making such a garment. Reference to the Figures shall be made in describing various embodiments of the invention. It should be noted that the embodiments depicted in the Figures and described herein are merely representative examples of the method of the invention. The various embodiments of the invention are suitable for use in conjunction with disposable absorbent garments such as refastenable adult incontinence underwear, prefastened disposable diapers, refastenable disposable training pants or swim pants, refastenable disposable enuresis garments, and the like. For illustration purposes, various embodiments of the present method invention shall be described in conjunction with refastenable incontinence or enuresis underwear.

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Disposable" refers to articles which are designed to be discarded after a limited use rather than being laundered or otherwise restored for reuse.

"Elastomeric" refers to a material or composite which can be elongated by at least 50% of its relaxed length and which will recover, upon release of the applied force, at least 20% of its elongation. It is generally preferred that the elastomeric material or composite be capable of being elongated by at least 100%, more preferably by at least 200%, of its relaxed length and recover, upon release of an applied force, at least 50% of its elongation.

"Longitudinal" and "transverse" have their customary meaning, as indicated by the longitudinal and transverse axes depicted in the Figures. The longitudinal axis lies in the plane of the article and is generally parallel to a vertical plane that bisects a standing wearer into left and right body halves when the article is worn. The transverse axis lies in the plane of the article generally perpendicular to the longitudinal axis.

These terms may be defined with additional language in the remaining portions of the specification.

Referring to FIGS. 1-7, the present invention in one aspect is directed to a refastenable disposable absorbent garment 10. In particular embodiments, the garment 10 defines a longitudinal direction 12, a longitudinal axis 11, a transverse direction 14, and a transverse axis 13. The garment defines longitudinally spaced apart first and second waist edges 16, 18. Each waist edge 16, 18 extends generally in the transverse direction 14. In particular embodiments, the first waist edge 16 is a front waist edge, corresponding to the front of the wearer, and the back waist edge 18 is a back waist edge, corresponding to the back of the wearer. In other embodiments, the first and second waist edges 16, 18 instead correspond to back and front waist edges, respectively, as representatively illustrated in FIGS. 1 and 2.

The garment includes a first waist region 20 contiguous with the first waist edge 16. The first waist region 20 defines first and second side edges 22, 24 spaced apart from each other in the transverse direction 14. The first waist region 20 defines a first surface 26 and an opposing second surface 28. The first surface 26 can be a body-facing surface and the second surface 28 can be a clothing-facing surface, as representatively illustrated in FIGS. 1-7; alternatively, the first surface 26 can be a clothing-facing surface and the second surface 28 can be a body-facing surface. The garment further includes a second waist region 40 contiguous with the second waist edge 18. The second waist region 40 and defining first and second side edges 42, 44 spaced apart from each in the transverse direction 14. The second waist region defines a first surface 46 and an opposing second surface 48. The first surface 46 can be a body-facing surface and the second surface 48 can be clothing-facing surface; alternatively, the first surface 46 can be a clothing-facing surface and the second surface 48 can be a body-facing surface.

In particular embodiments, the first waist region 20 is a front waist region, corresponding to the front of the wearer, and the second waist region 40 is a back waist edge, corresponding to the back of the wearer. In other embodiments, the first and second waist regions 20, 40 instead correspond to back and front waist regions, respectively, as representatively illustrated in FIGS. 1 and 2. The garment further includes a crotch region 50 that extends between and interconnects the first waist region 20 and the second waist region 40. The crotch region 50 can include an absorbent composite 49, such as an absorbent composite constructed of a fluid-absorbent core 45 of fluff and/or superabsorbent polymer sandwiched between a bodyside topsheet and a non-bodyside backsheet. Such absorbent composites are known in the art.

The first waist region 20 is elastomeric at least in the region proximal the first side edge 22 and also in the region proximal the second side edge 24 of the first waist region 20. The second waist region 40 is elastomeric at least in the region proximal the first side edge 42 and also in the region proximal the second side edge 44 of the second waist region 40. In particular embodiments, the first waist region 20 is substantially continuously transversely elastomeric from the first side edge 22 to the second side edge 24. Similarly, in particular embodiments, the second waist region 40 is substantially continuously transversely elastomeric from the first side edge 42 to the second side edge 44. In evaluating whether a waist region is substantially continuously transversely elastomeric, the regions to which any fastening component (described below) or absorbent composite is attached, or within which bonds or seams are present, are ignored. In particular embodiments, the first waist region 20, the second waist region 40, or both, comprise an elastomeric nonwoven material, and preferably consists essentially of an elastomeric nonwoven material. In particular embodiments, the elastomeric nonwoven material comprises an elastomeric film sandwiched between two nonwoven facing layers. U.S. Pat. No. 7,803,244 issued Sep. 28, 2010 to Siqueira et al. and assigned to Kimberly-Clark Worldwide, Inc. discloses particular examples of elastomeric nonwoven composites suitable for use in particular embodiments of the present invention.

Figure 1:
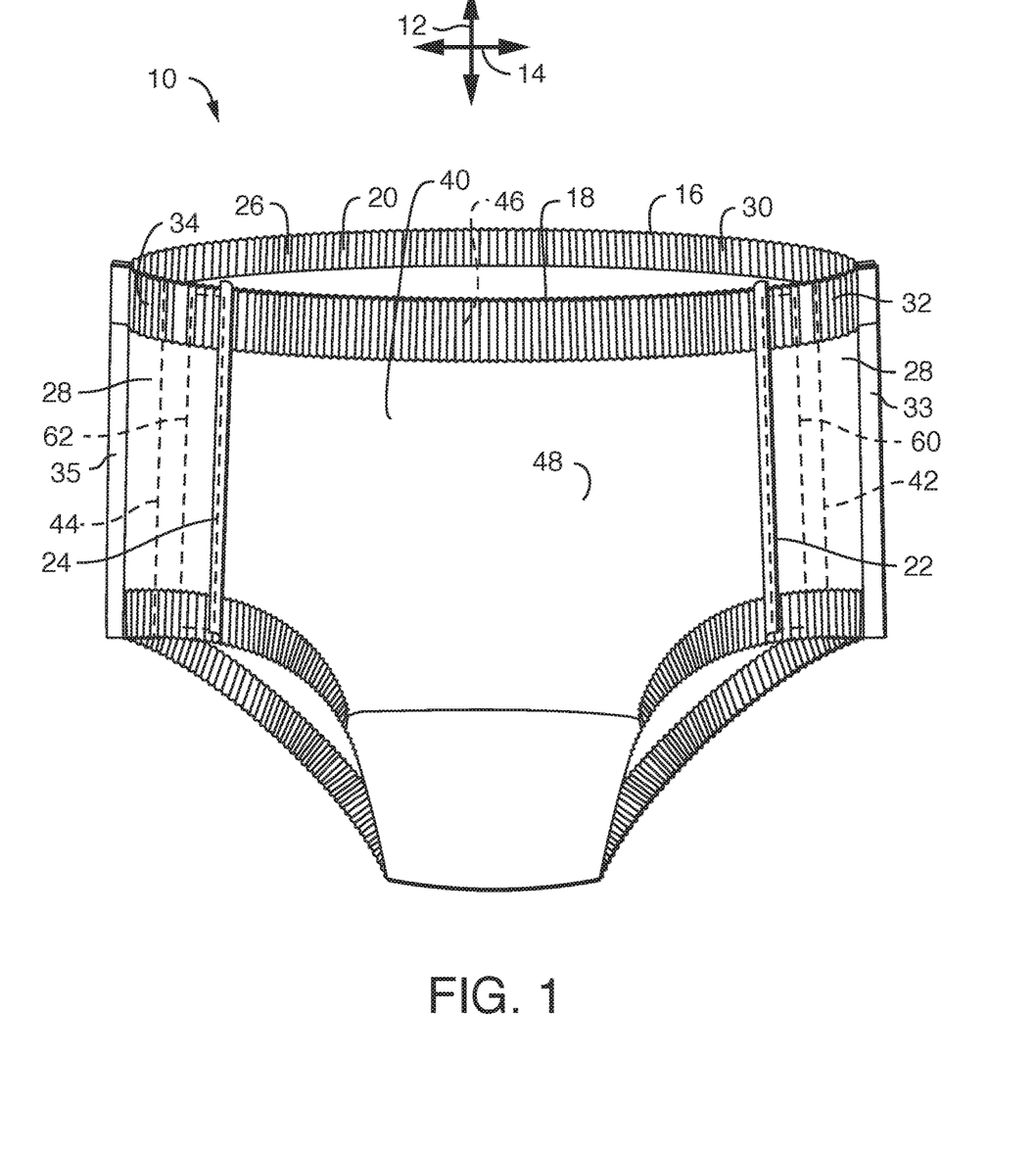
FIG. 1 depicts a front perspective view of one example of a garment of the present invention, the garment shown in a prefastened, pant-like configuration.

In particular embodiments, the first waist region 20 is formed by a unitary member that extends from the first side edge 22 of the first waist region 20 to the second side edge 24 of the first side region 20. Such an embodiment is depicted in FIG. 9. In other embodiments, the first waist region is formed by bonding together multiple pieces of material. For example, in the embodiment of FIGS. 1-2 and 8, the first waist region 20 (which is depicted as a back waist region) is comprised of a center section (such as a relatively wide center section 30), a first side section 32, and a second side section 34. The first side section 32 is attached to the center section 30 along a first side seam 33, and the second side section 34 is attached to the center section 30 along a second side seam 35. In such an embodiment, when the garment 10 is positioned on a wearer, the side seams 33, 35 align generally with the hips of the wearer. Note that in the embodiments of FIGS. 1-2, the first (back) waist region 20 of the garment 10, when configured in a pant-like configuration as shown in FIG. 1, would actually extend forward past the hip area to partially wrap around the front waist section of the wearer. In other words, the first and second side section 32, 34 are considered a part of the first (back) waist region, even though they are positioned on the front waist section of the wearer when the garment is donned.

Figure 10:
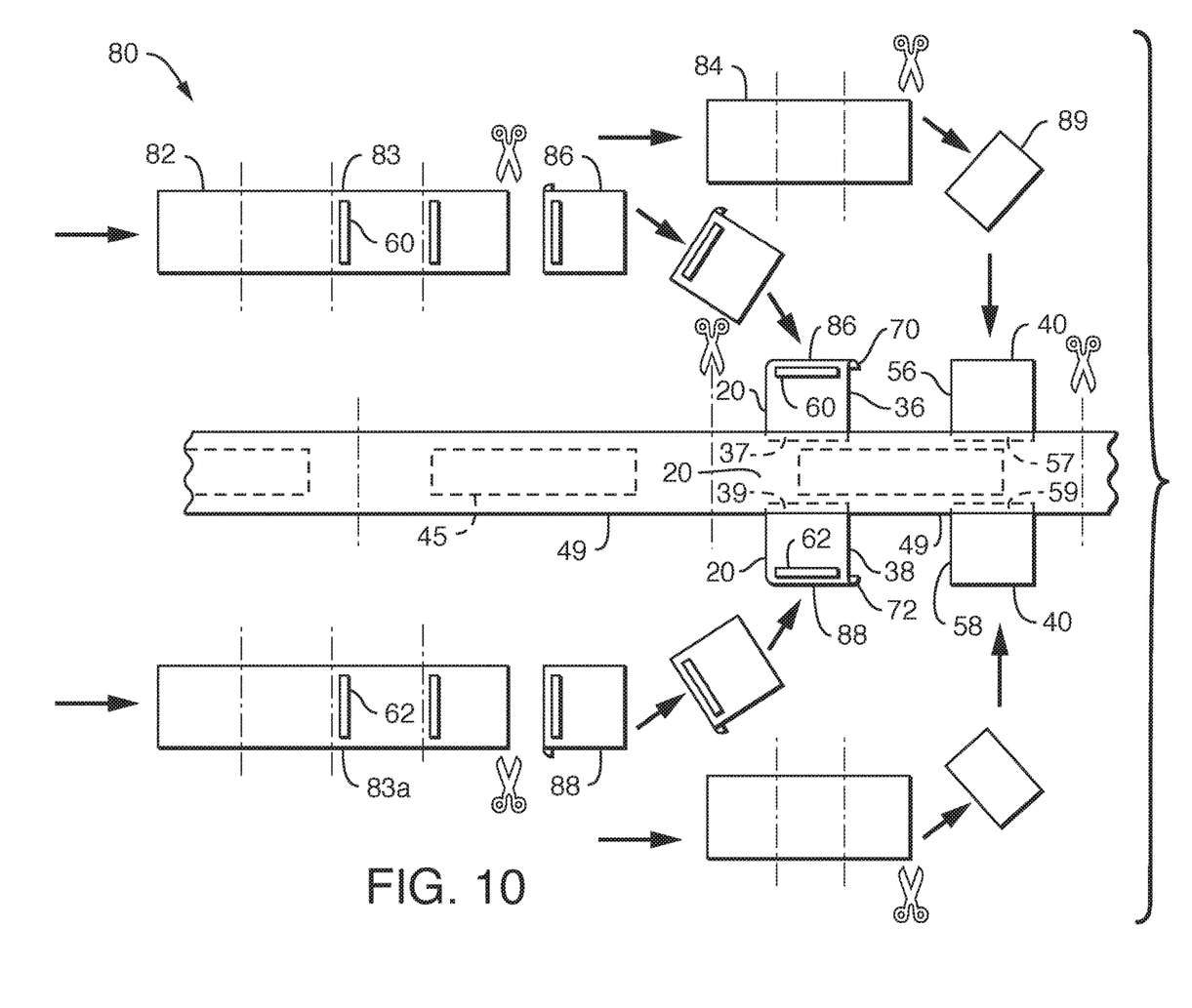
FIG. 10 depicts a top view of yet another embodiment of the method aspect of the present invention.
Figure 11:
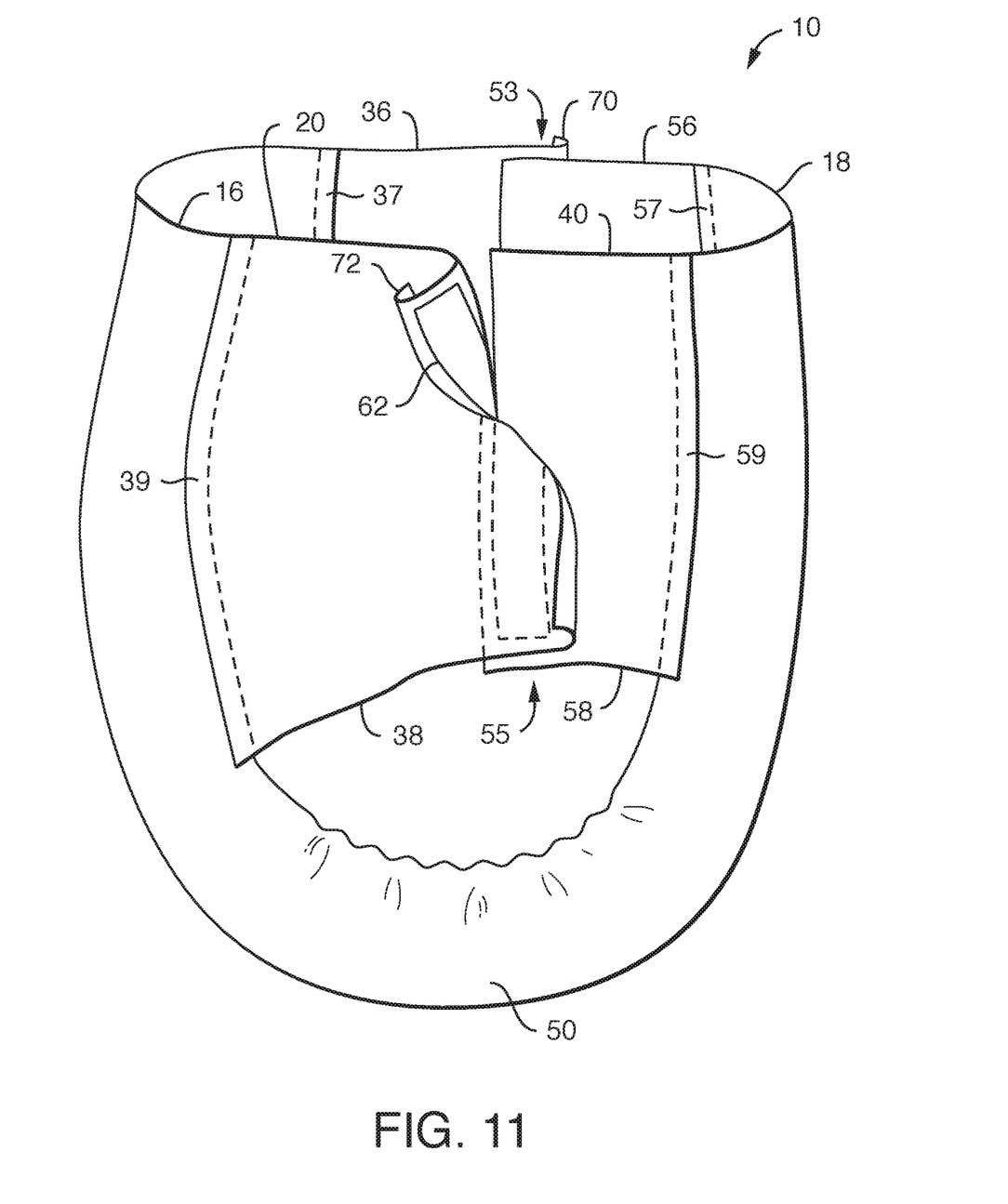
FIG. 11 depicts a side perspective view of another example of a garment of the present invention, the garment shown in a partially prefastened, pant-like configuration.

In an alternative embodiment, the first waist region 20 is formed by bonding opposing first and second side panels 36 and 38 to a central absorbent composite 49 along bond regions 37 and 39, as representatively illustrated in FIGS. 10-11. Similarly, the second waist panel is formed by bonding opposing third and fourth side panels 56 and 58 to the central absorbent composite 49 along bond regions 57 and 59. Such a garment may be made into a pant-like configuration by joining the side panels 36 and 38 to the side panels 56 and 58 along a pair of refastenable side seams 53, 55, as representatively illustrated in FIG. 11. In particular embodiments, each side panel, 36/38/56/58 comprises an elastomeric nonwoven material, and preferably consists essentially of an elastomeric nonwoven material. In particular embodiments, the central absorbent composite 49 comprises an absorbent core 45 sandwiched between a body-side topsheet layer and a non-bodyside backsheet layer.

The garment 10 further comprises a non-extensible rigid first fastening component 60 attached to the first surface 26 of the first waist region 20 adjacent its first side edge 22, and further comprises a non-extensible, relatively rigid second fastening component 62 attached to the first surface 26 of the first waist region 20 adjacent its second side edge 24. "Non-extensible" as used herein means unable to be elongated by more than 20% without permanent rupture or permanent deformation. In particular embodiments, each fastening component 60, 62 is relatively rigid. "Relatively rigid" means more rigid than the substrate to which the fastening component is directly attached. The first fastening component 60 defines a length 61, and the second fastening component 62 defines a length 63. Example of suitable fastening components include but are not limited to mechanical fasteners, such as hook or mushroom type fastening components. The first waist region 20 defines a first flange portion 70 positioned transversely outward of the first fastening component 60, and further defines a second flange portion 72 positioned transversely outward of the second fastening component 62. "Transversely outward" as used herein means transversely distal to a longitudinally extending centerline 11 of the refastenable garment when the garment is in an unfastened, laid-open condition, as representatively illustrated in FIG. 2, but with any permanent side seams still intact. In particular embodiments, a secondary fastener or disposal tab (not shown) is connected to the flange portion, and may or may not extend transversely outward from the flange portion.

The first flange portion 70 is transversely curled toward the second surface 28 of the first waist region 20 along a first flange portion curled length 71, and the second flange portion 72 is transversely curled toward the second surface 28 of the first waist region 20 along a second flange portion curled length 73. "Curled toward the second surface of the first waist region" as used herein means biased away from an imaginary flat plane occupied by the majority of the first waist region to form a concavity in the second surface and a convexity in the first surface of the first waist region, when the garment is in an unfastened, laid-open, relaxed condition. Each flange portion 70, 72 can be curled along any suitable portion of its length, including 100% of its length. In one embodiment, the first flange portion curled length 71 is at least 25% of the length 61 of the first fastening component 60, and the second flange portion curled length 73 is at least 25% of the length 63 of the second fastening component 62. In another embodiment, the first flange portion curled length 71 is at least 90% of the length 61 of the first fastening component 60, and the second flange portion curled length 73 is at least 90% of the length 63 of the second fastening component 62. In particular embodiments, first and second flange portion curled lengths 71, 73 are each at least eight centimeters. (If a flange portion 70, 72 exhibits curling along two or more length sections, separated by one or more portions along the length that exhibit(s) no curling, then the curled length 71, 73 of such flange portion is the sum of the curled lengths of the individually curled length sections.)

In particular embodiments, each flange portion 70, 72 defines a transverse width 75, defined as the transverse distance from the transversely outward-most edge of the fastening component 60, 62 to the closest side edge 22, 24 when the flange portion 70, 72 is straightened out to a laid-flat but unstretched condition. For example, in FIG. 6, the second flange portions 72 defines a transverse width 75 (shown straightened, laid flat, and unstretched in phantom lines). In particular embodiments, the average transverse width of the first flange portion and the average transverse width of the second flange portion are each between 5 millimeters and 12 millimeters.

Figure 5:
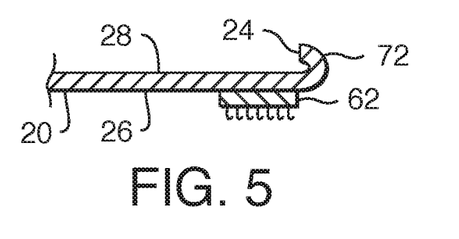
FIG. 5 depicts a cross-sectional view of the embodiment of FIG. 3, taken along line 5-5.
Figure 6:
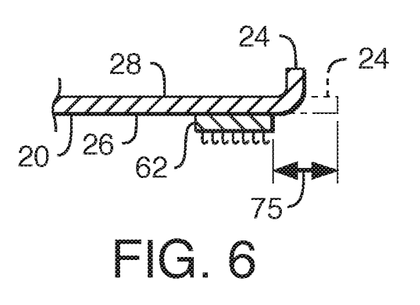
FIG. 6 depicts a variation of the embodiment depicted in FIG. 5.
Figure 7:
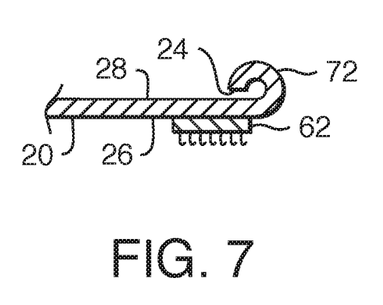
FIG. 7 depicts another variation of the embodiment depicted in FIG. 5.

In particular embodiments, the first flange portion 70 is transversely curled toward the second surface 28 of the first waist region 20 by at least 90 degrees along at least a portion of (such as all of) the first flange portion curled length 71. Similarly, in particular embodiments, the second flange portion 72 is transversely curled toward the second surface 28 of the first waist region 20 by at least 90 degrees along at least a portion of (such as all of) the second flange portion curled length 73. FIG. 6 representatively illustrates a cross-section of a flange portion 72 that is curled toward the second surface 28 by approximately 90 degrees. In other embodiments, the first flange portion 70 is transversely curled toward the second surface 28 of the first waist region 20 by at least 180 degrees along at least a portion of (such as all of) the first flange portion curled length 71, and the second flange portion 72 is transversely curled toward the second surface 28 of the first waist region 20 by at least 180 degrees along at least a portion of (such as all of) the second flange portion curled length 73. FIG. 5 representatively illustrates a cross-section of a flange portion 72 that is curled toward the second surface 28 by approximately 180 degrees. FIG. 7 representatively illustrates a cross-section of yet another example in which the flange portion 72 is curled toward the second surface 28 by over 180 degrees (such as approximately 270 degrees, as shown). The degree of curl is determined via visual examination when the garment is in an unfastened, laid-open, relaxed condition. Advantageously, it has been discovered that by employing a curled flange portion next to a fastening component that lies relatively close to an edge of the underlying base substrate, the refastenable seam or fastening portion can in particular embodiments become easier to see and/or easier to grasp.

Figure 8:
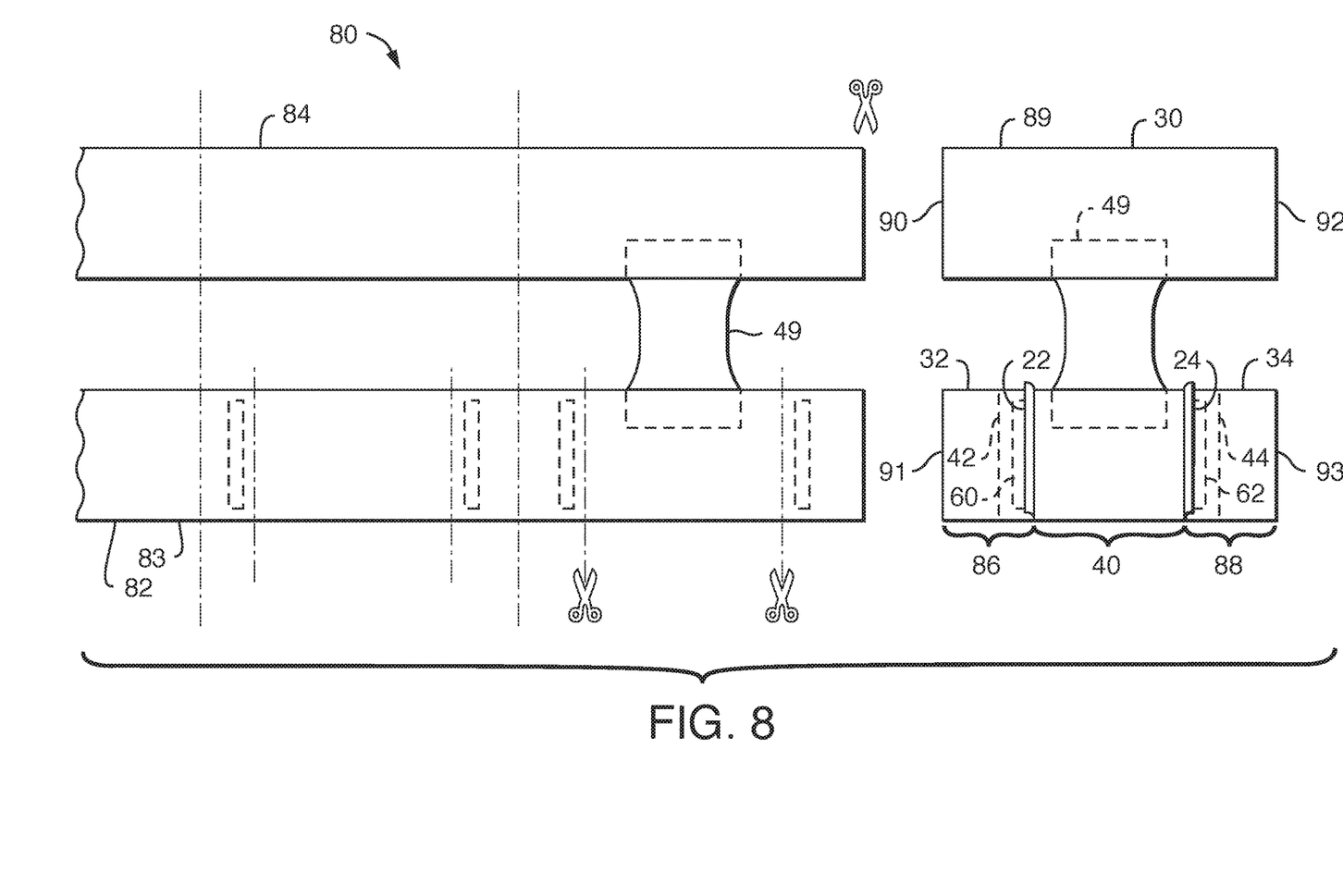
FIG. 8 depicts a top view of one embodiment of the method aspect of the present invention.
Figure 9:
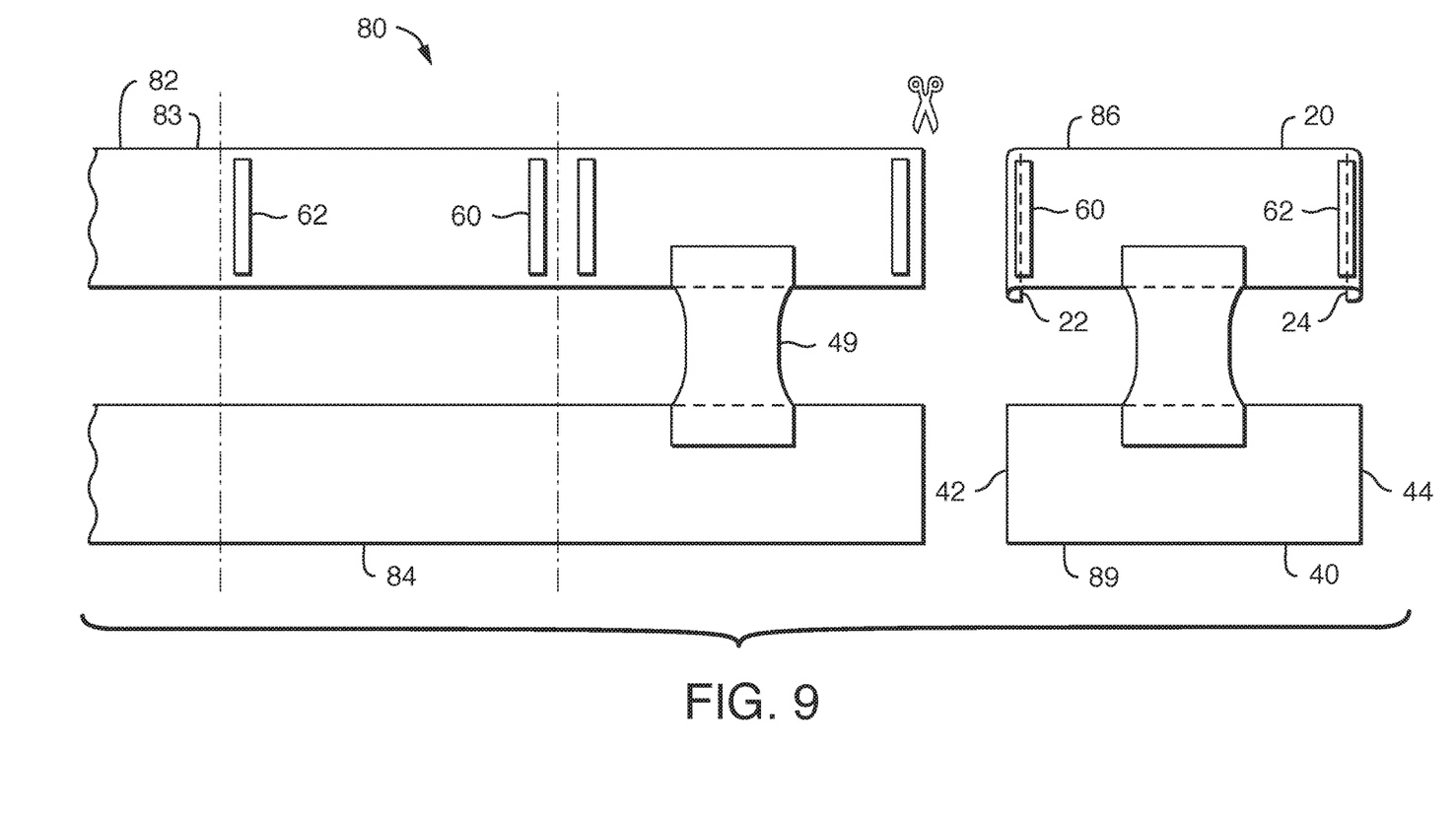
FIG. 9 depicts a top view of one another of the method aspect of the present invention.

Referring to FIGS. 8-10, in another aspect the present invention is directed to a process 80 for making a refastenable disposable absorbent garment, such as the garment 10 described above. The process 80 includes providing at least a first elastomeric waist panel web 82. The elastomeric waist panel web can comprise an elastomeric nonwoven composite, and elastomeric film/nonwoven laminate, an elastomeric filament/nonwoven, or the like. The method 80 further includes stretching the elastomeric waist panel web by at least 10%, more particularly at least 50%, and still more particularly at least 90%, to create a stretched waist panel web 83. The method 80 further comprises attaching a non-extensible, relatively rigid first fastening component 60 to the stretched waist panel web 83. The method further includes severing (such as by cutting) the first waist panel web 82 adjacent the first fastening component 60 to create a first waist region first portion 86. The method further includes incorporating the first waist region first portion 86 into a first waist region 20 of the garment 10.

As with particular embodiments of the garment described above, the garment resulting from particular embodiments of the process defines a first flange portion 70 transversely outward of the first fastening component 60. The first flange portion 70 is transversely curled toward a second surface 28 of the first waist region 20 along a first flange portion curled length 71.

The first waist region first portion 86 can comprise the entirety of the first waist region 20, or can comprise only a part of the first waist region 20. For example, in the embodiment representatively illustrated in FIG. 9, the first waist region first portion 86 comprises the entirety of the first waist region 20, such that the first waist region 20 is defined by a unitary member that extends from the first side edge 22 of the first waist region 20 to the second side edge 24 of the first side region 20. Alternatively, in the embodiments of FIGS. 8 and 10, the first waist region first portion 86 comprises only one side part of the first waist region 20.

Still referring to FIGS. 8 and 9, in particular embodiments the process further comprises attaching a non-extensible second fastening component 62 to a stretched waist panel web, such as to the same stretched waist panel web 83 (FIGS. 8 and 9), or to an additional waist panel web 83a (FIG. 10). The process in this embodiment further includes severing the waist panel web 83/83a adjacent the second fastening component to create a first waist region second portion 88, and incorporating the first waist region second portion 88 into the first waist region 20 of the garment 10. As with particular embodiments of the garment described above, the garment resulting from particular embodiments of the process defines a second flange portion 72 transversely outward of the second fastening component 62. The second flange portion 70 is transversely curled toward a second surface 28 of the first waist region 20 along a second flange portion curled length 73.

In particular embodiments, the process 80 further comprises providing a second waist panel web, such as a second elastomeric waist panel web 84. The second elastomeric waist panel web 84 can comprise an elastomeric nonwoven composite, and elastomeric film/nonwoven laminate, an elastomeric filament/nonwoven, or the like. The method 80 can further includes stretching the second elastomeric waist panel web by at least 10%, more particularly at least 50%, and still more particularly at least 90%. The method 80 can further comprise attaching a mating fastening component or components (not shown) to the second waist panel web 84. The method further includes severing (such as by cutting) the second waist panel web 84 to create a second waist region portion 89. The method further includes incorporating the second waist region portion 89 into a second waist region 40 of the garment 10.

Figure 2:
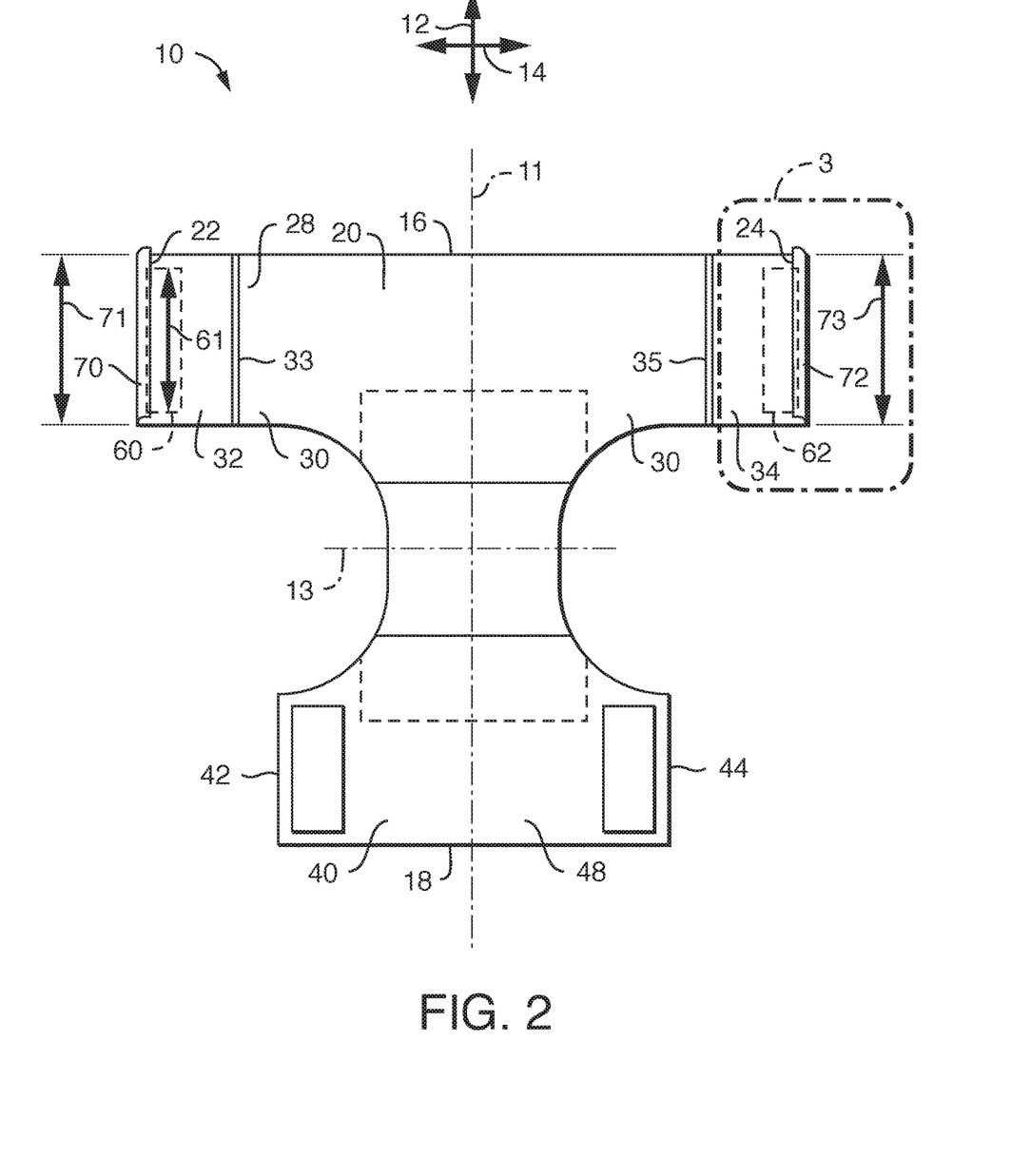
FIG. 2 depicts a plan view of the garment of FIG. 1, the garment shown in an unfastened, laid-open, relaxed configuration.
Figure 3:
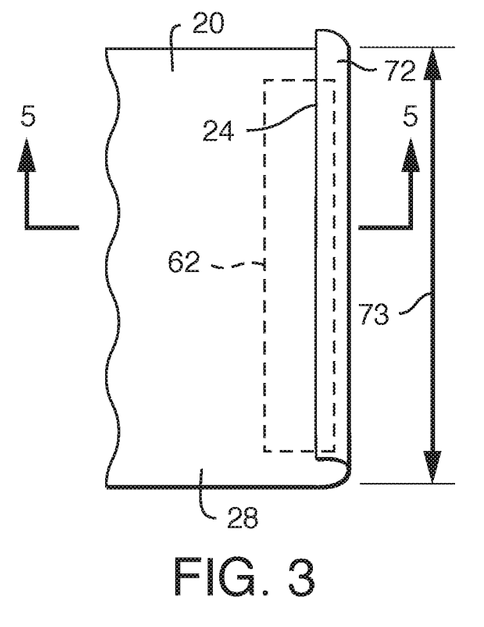
FIG. 3 depicts a close-up perspective view of a portion of the garment of FIG. 2.
Figure 4:
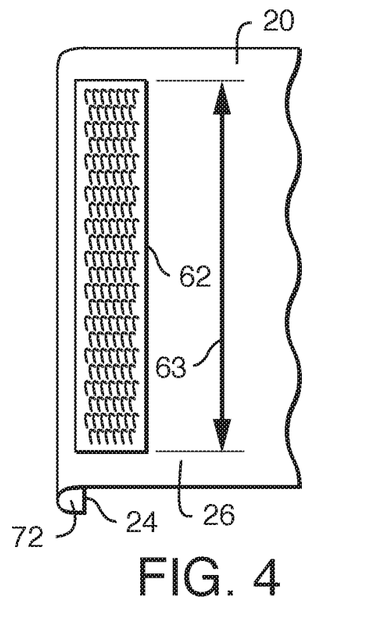
FIG. 4 depicts a close-up perspective view of the same portion of the garment depicted in FIG. 3, but as view from the reverse surface of the garment.

In the process embodiment of FIG. 8, edges 90, 92 may be permanently bonded to edges, 91, 93, respectively, to form the pant-like configuration representatively illustrated in FIGS. 1-2 as a garment 10 having side seams 33, 35. In the process embodiment of FIG. 9, the fastening components 60, 62 may be refastenably engaged with the second waist region 40 in close proximity to the first and second side edges 42, 44, respectively, to form a garment having a pant-like configuration. In the process embodiment of FIG. 10, the fastening component 60 can be refastenably engaged to the third side panel 56 and the fastening component 62 can be refastenably engaged to the fourth side panel 58 to form a garment having the pant-like configuration representatively illustrated in FIG. 11 as a pant-like garment 10.

Without wishing to be bound by any particular theory, it is believed that by attaching a non-extensible, and preferably relatively rigid fastening component to certain elastomeric webs while such webs are stretched in a certain manner in accordance with the process aspect of the present invention, and by subsequently severing such webs in close proximity to an edge of the fastening component, desired degrees of curl can be imparted to the elastomeric web, creating a curled flange portion. Furthermore, it is believed that the amount of curl imparted to the flange portion is directly proportional (though necessarily linearly so) to the amount of stretch/elongation to which the elastomeric web is subjected during such attaching. Advantageously, it has been discovered that by employing a curled flange portion next to a fastening component that lies relatively close to an edge of the underlying base substrate, the refastenable seam or fastening portion of a garment incorporating such structure can in particular embodiments become easier to see and/or easier to grasp.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A process for making a refastenable disposable absorbent garment, the garment defining a longitudinal axis extending in a longitudinal direction and a transverse axis extending in a transverse direction, the garment further comprising longitudinally spaced apart first and second waist edges extending generally in the transverse direction, the process comprising:
providing an elastomeric waist panel web;
stretching the elastomeric waist panel web by at least 10% to create a stretched waist panel web;
attaching a non-extensible, relatively rigid first fastening component to the stretched waist panel web;
severing the waist panel web adjacent the first fastening component to create a first waist region first portion;
incorporating the first waist region first portion into a first waist region of the garment,
wherein the first waist region is contiguous with the first waist edge, the first waist region defining a first side edge extending in the longitudinal direction, the first waist region defining opposed first and second surfaces, wherein the first waist region is elastomeric proximal the first side edge of the first waist region,
the first fastening component being attached to the first surface of the first waist region adjacent its first side edge, the first fastening component having a length,
wherein the first waist region defines a first flange portion transversely outward of the first fastening component,
wherein the first flange portion is transversely curled toward the second surface of the first waist region along a first flange portion curled length.

2. The process of claim 1 further comprising:
attaching a non-extensible, relatively rigid second fastening component to the stretched waist panel web;
severing the waist panel web adjacent the second fastening component to create a first waist region second portion;
incorporating the first waist region second portion into the first waist region of the garment,
wherein the first waist region further defines a second side edge spaced apart from the first side edge in the transverse direction, wherein the first waist region is elastomeric proximal the first side edge and the second side edge of the first waist region,
the second fastening component being attached to the first surface of the first waist region adjacent its second side edge, the second fastening component having a length,
wherein the first waist region defines a second flange portion transversely outward of the second fastening component,
wherein the second flange portion is transversely curled toward the second surface of the first waist region along a second flange portion curled length.

3. The process of claim 1, the garment further comprising a second waist region contiguous with the second waist edge and defining first and second side edges spaced apart in the transverse direction, the garment further comprising a crotch region that extends between and interconnects the first and second waist regions.

4. The process of claim 3, wherein the first and second flange portions each define a transverse width, wherein the transverse width of the first flange portion and the transverse width of the second flange portion are each between 5 millimeters and 12 millimeters.

5. The process of claim 3, wherein the first flange portion curled length is at least 25% of the length of the first fastening component, and wherein the second flange portion curled length is at least 25% of the length of the second fastening component.

6. The process of claim 5, wherein the first flange portion is transversely curled toward the second surface of the first waist region by at least 90 degrees along the first flange portion curled length, and wherein the second flange portion is transversely curled toward the second surface of the first waist region by at least 90 degrees along the second flange portion curled length.

7. The process of claim 6, wherein the first flange portion is transversely curled toward the second surface of the first waist region by at least 180 degrees along the first flange portion curled length, and wherein the second flange portion is transversely curled toward the second surface of the first waist region by at least 180 degrees along the second flange portion curled length.

8. The process of claim 5, wherein the first flange portion curled length is at least 90% of the length of the first fastening component, and wherein the second flange portion curled length is at least 90% of the length of the second fastening component.

9. The process of claim 1, wherein the first surface is a body-facing surface.

10. The process of claim 1, wherein the first waist region is a back waist region.

* * * * *